(12) United States Patent
Al-Sabah et al.

(10) Patent No.: US 10,697,164 B1
(45) Date of Patent: *Jun. 30, 2020

(54) SANITIZING AND SMART SMELL DETECTION DEVICE FOR HANDHELD BIDET SPRAYER AND AIR FRESHENING

(71) Applicants: Sabah Thamer Abdullah S. Al-Sabah, Safat (KW); Mohammad Salman Mohammad Salman Al-Sabah, Safat (KW); Fahad S. F. S. A. Al-Sahli, Safat (KW)

(72) Inventors: Sabah Thamer Abdullah S. Al-Sabah, Safat (KW); Mohammad Salman Mohammad Salman Al-Sabah, Safat (KW); Fahad S. F. S. A. Al-Sahli, Safat (KW)

( * ) Notice: Subject to any disclaimer, the term of this patent is extended or adjusted under 35 U.S.C. 154(b) by 0 days.

This patent is subject to a terminal disclaimer.

(21) Appl. No.: 16/734,099

(22) Filed: Jan. 3, 2020

Related U.S. Application Data

(63) Continuation of application No. 16/526,179, filed on Jul. 30, 2019, now Pat. No. 10,557,257.

(51) Int. Cl.
   *E03D 9/00* (2006.01)
   *A61L 2/22* (2006.01)
   (Continued)

(52) U.S. Cl.
   CPC .............. *E03D 9/002* (2013.01); *A61L 2/10* (2013.01); *A61L 2/22* (2013.01); *E03D 9/085* (2013.01);
   (Continued)

(58) Field of Classification Search
   CPC ... A61L 2/10; A61L 2/22; E03D 9/002; E03D 9/085
   See application file for complete search history.

(56) References Cited

U.S. PATENT DOCUMENTS 5,987,659 A   11/1999   Cannizzaro
5,991,937 A   11/1999   Safara
(Continued)

FOREIGN PATENT DOCUMENTS

KR   101797163 B1   12/2017

OTHER PUBLICATIONS

"Handheld Bidet Sprayer for Toilet," (c) 1996-2018. Amazon.com website, any identified foreign patents and/or publications were properly submitted in parent U.S. Appl. No. 16/526,179, filed Jul. 30, 2019, the priority of which is claimed.

*Primary Examiner* — Sean E Conley
(74) *Attorney, Agent, or Firm* — Richard C. Litman; Nath, Goldberg & Meyer

(57) ABSTRACT

A sanitizing device for a handheld bidet sprayer includes a housing for holding a handheld bidet sprayer on a spray head mount, an optical sensor used to detect the presence or absence of the sprayer in the housing, an odoriferous substance sensor used to sense odoriferous conditions or indications of a significant presence of microbes, a chemical discharge module, an ultraviolet light source, and a control module. The chemical discharge module includes a chemical supply holder and a plurality of conduits extending from the chemical supply holder. The chemical supply holder includes at least one container of fragrance and at least one container of sanitizer. Upon sensing odoriferous conditions or indications of a significant presence of microbes, the control module causes the discharge of the sanitizer and/or fragrance.

6 Claims, 7 Drawing Sheets

(51) Int. Cl.
*E03D 9/08* (2006.01)
*A61L 2/10* (2006.01)

(52) U.S. Cl.
CPC ........ *A61L 2202/11* (2013.01); *A61L 2202/14* (2013.01)

(56) References Cited

U.S. PATENT DOCUMENTS

| | | |
|---|---|---|
| 7,543,339 B1 | 6/2009 | Harris |
| 10,557,257 B1 * | 2/2020 | Al-Sabah .................. A61L 2/10 |
| 2005/0246828 A1 | 11/2005 | Shirai et al. |
| 2007/0256226 A1 | 11/2007 | Pinizzotto |
| 2015/0337525 A1 | 11/2015 | Bailey |
| 2018/0021465 A1 | 1/2018 | Dobrinsky et al. |
| 2018/0238038 A1 | 8/2018 | Pomeroy et al. |

* cited by examiner

SANITIZING AND SMART SMELL DETECTION DEVICE FOR HANDHELD BIDET SPRAYER AND AIR FRESHENING

CROSS REFERENCE TO RELATED APPLICATIONS

This application is a continuation of application Ser. No. 16/526,179, filed Jul. 30, 2019, pending, the priority of which is claimed.

BACKGROUND

1. Field

The disclosure of the present patent application relates to a sterilization device, and particularly, to a device for sterilizing a handheld bidet sprayer.

2. Description of the Related Art

A bidet generally refers to a plumbing fixture that can be used for washing the genitals and anal area after using the toilet. In some instances, the bidet includes a fixture that is integrated with the toilet. In other instances, the bidet includes a separate fixture or appliance, such as a washing basin or a handheld sprayer next to the toilet.

Because of the manner in which the handheld bidet sprayer is used, the handheld bidet sprayer can be susceptible to accumulation of microbial growth. This is particularly the case when the bidet sprayer is used in a public space, such as a restaurant. Thus, a device for sterilizing a handheld bidet sprayer solving the aforementioned problems is desired.

SUMMARY

A sanitizing device for a handheld bidet sprayer includes a housing for holding a handheld bidet sprayer on a spray head mount, an optical sensor used to detect the presence or absence of the sprayer in the housing, an odoriferous substance sensor used to sense odoriferous conditions or indications of a significant presence of microbes, a chemical discharge module, an ultraviolet light source, and a control module. The chemical discharge module includes a chemical supply holder and a plurality of conduits extending from the chemical supply holder. Each conduit is connected to a container of fragrance or a container of sanitizer in the chemical supply holder. Upon sensing odoriferous conditions or indications of a significant presence of microbes, the sanitizer and/or fragrance is discharged.

Sanitization of the primary spray head can be further provided by the ultraviolet light source. The ultraviolet light source can include an ultraviolet lamp and driver circuit for powering the ultraviolet light lamp. During a sanitation cycle, the ultraviolet light source provides surface sterilization of the handheld bidet sprayer.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
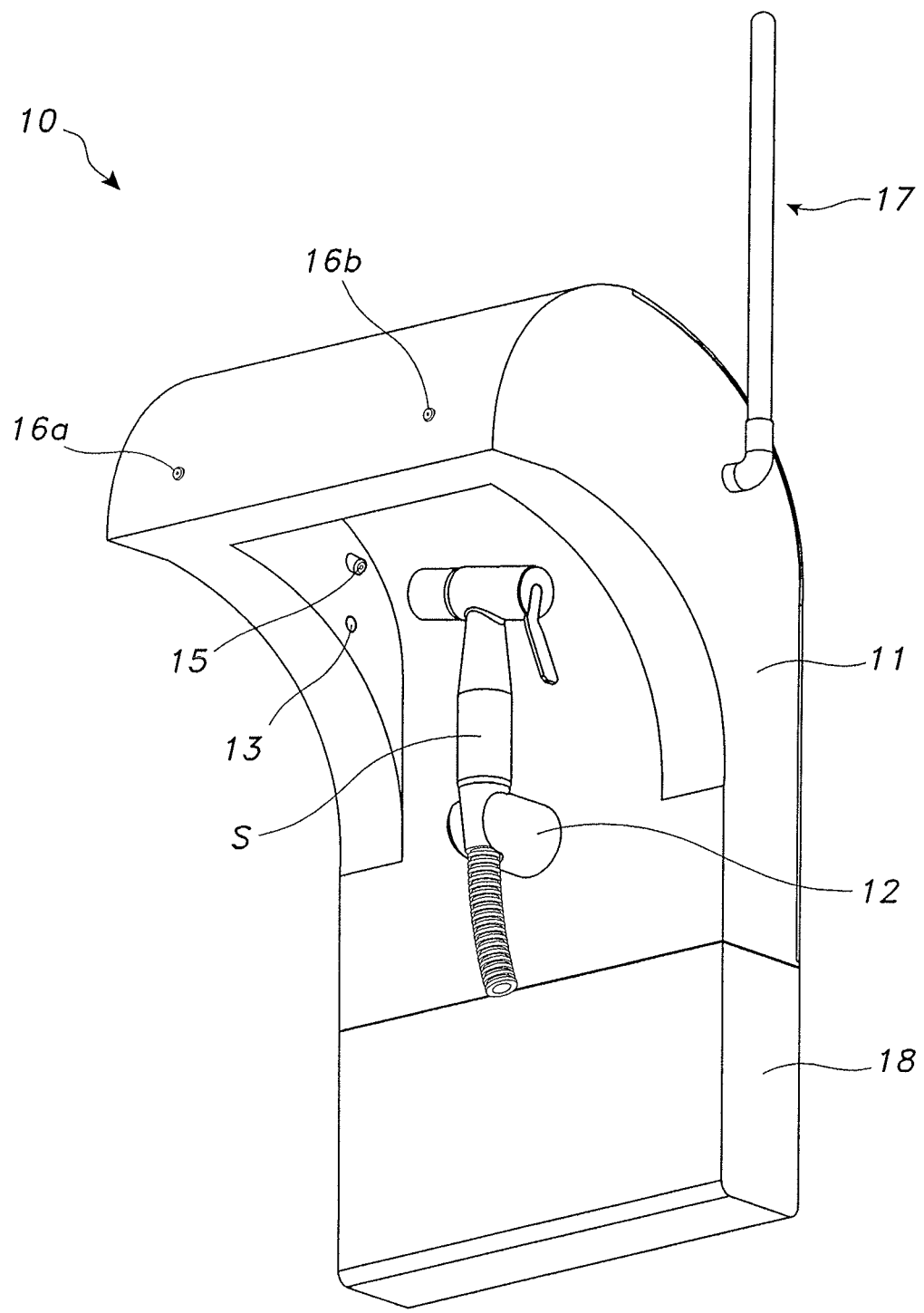
FIG. 1 is a perspective view of a sanitizing device for a handheld bidet sprayer.
Figure 2:
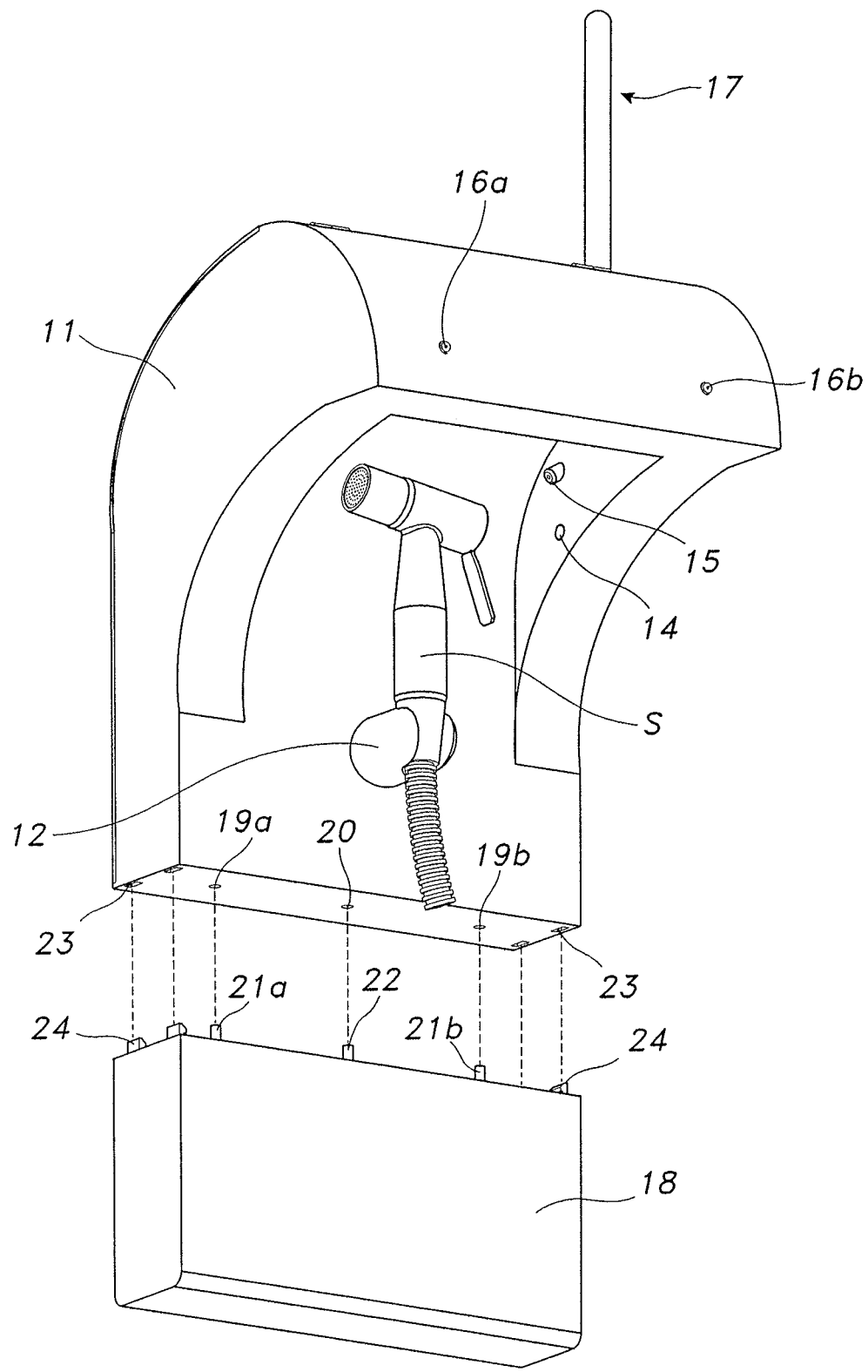
FIG. 2 is a partially exploded view of the sanitizing device for a handheld bidet sprayer.
Figure 3:
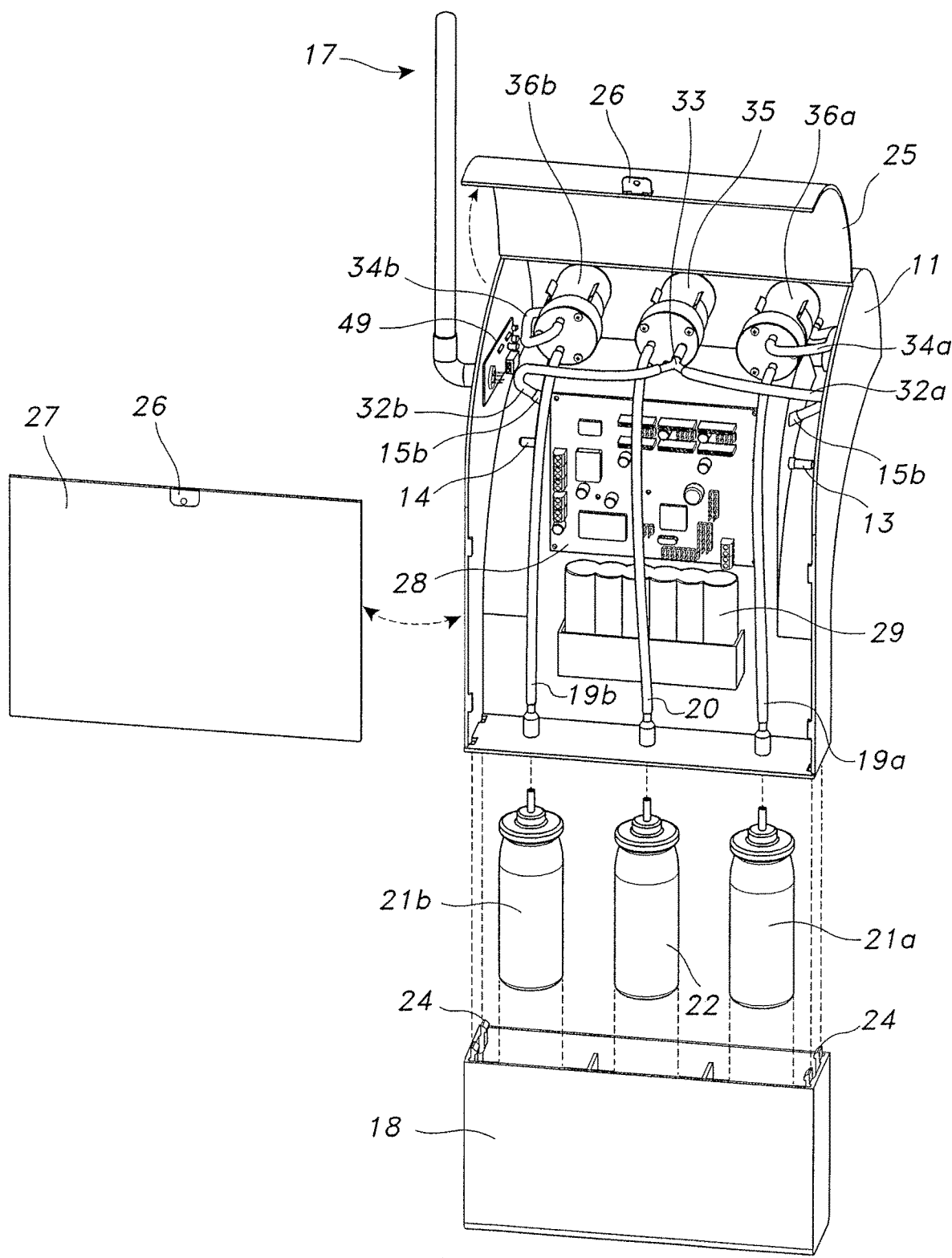
FIG. 3 is a partially exploded, partial view of an inner portion of the sanitizing device for a handheld bidet sprayer.
Figure 4:
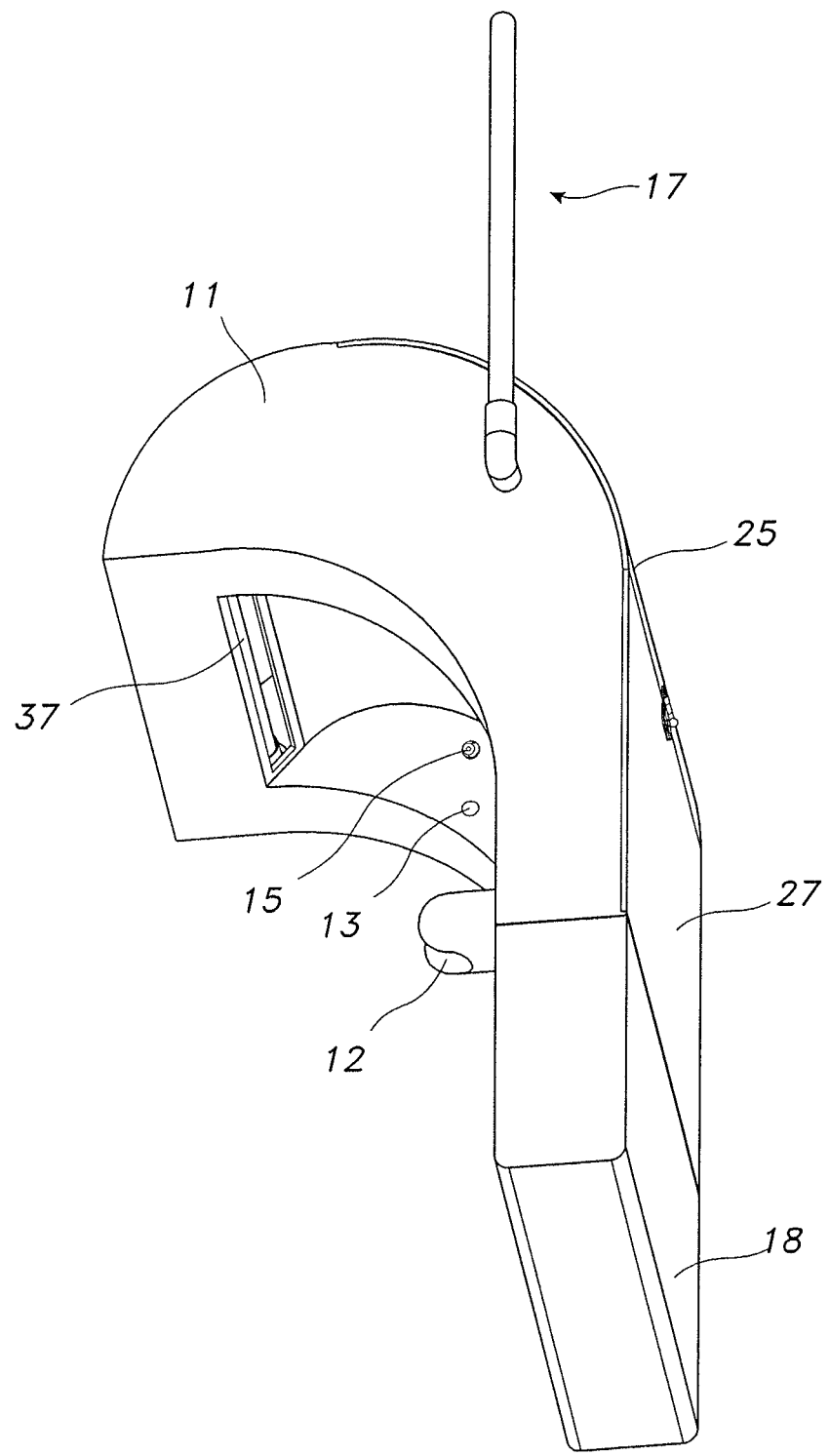
FIG. 4 is a side view of the sanitizing device for a handheld bidet sprayer, showing the ultraviolet lamp.

As shown in FIGS. 1-4, a sanitizing device for a handheld bidet sprayer 10 can include a housing 11 for holding a handheld bidet sprayer S on a spray head mount 12, an optical sensor 13 used to detect the presence or absence of the sprayer S in the housing 11, an optical transmitter 14, an odoriferous substance sensor 17 used to sense odoriferous conditions or indications of a significant presence of microbes, a chemical discharge module, an ultraviolet light source, and a control module 28. The housing can also include device cover 25, battery cover attachment 26, batteries 29, and battery cover 27. Also included in housing 11 is UV or germicidal light source 37. UV or germicidal light source 37 is also controlled by controller 28 and can also be used to sanitize the device itself.

The chemical discharge module includes a chemical supply holder 18 for storing one or more fragrance containers and sanitizer containers, conduits extending from the fragrance containers and sanitizer containers, and nozzles for dispensing the respective chemicals from the conduits. The chemicals can be any suitable sanitizers and fragrances which are compatible with the equipment. The use of fragrances allows conditioning of the air in response to different types of odors. The sanitizer can be used to sanitize the sprayer S. In an exemplary embodiment, the chemical supply holder houses fragrance containers 21a, 21b, and one sanitizer container 22. Conduit 19a is connected to fragrance container 21a and pump 36a, conduit 19b is connected to fragrance container 21b and pump 36b, and conduit 20 is connected fragrance container 22. Upon sensing odoriferous conditions or indications of a significant presence of microbes, the control module 28 causes the discharge of the sanitizer and/or fragrance through outlet nozzles 16a and/or 16b. Latches 23, 24 are used to mount chemical supply holder 18 to housing 11.

Figure 5:
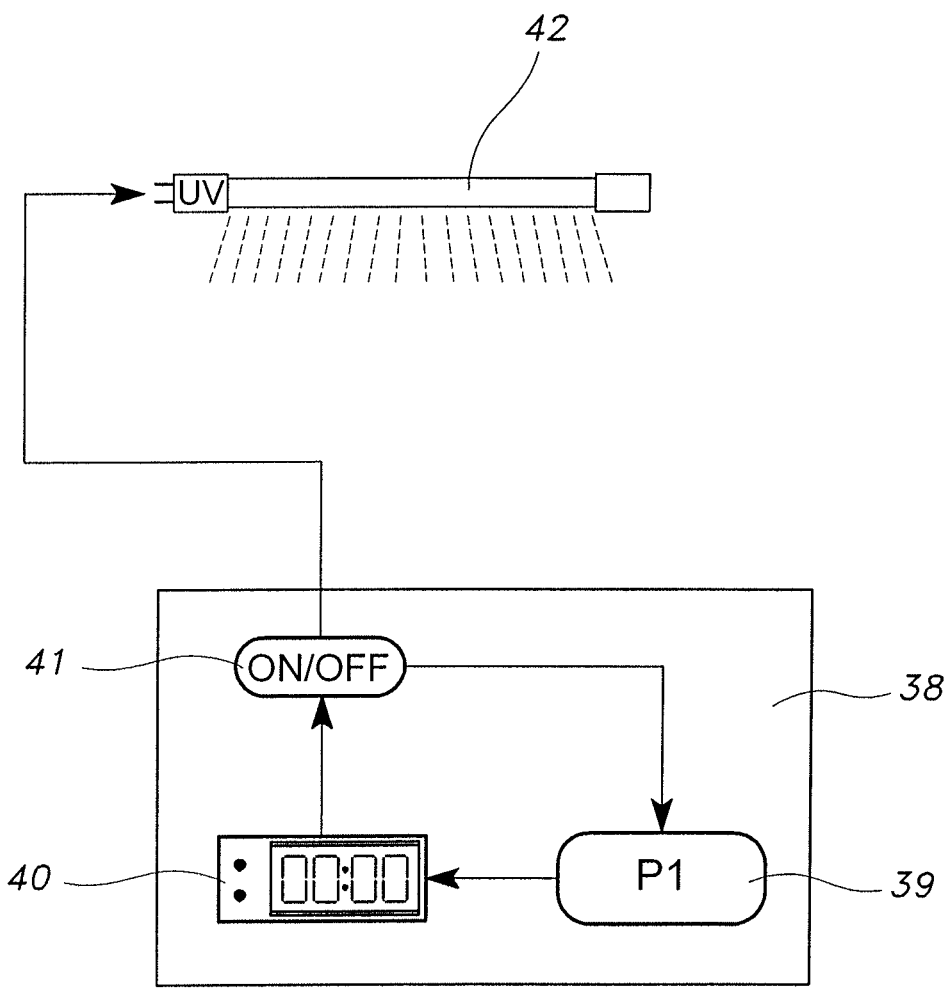
FIG. 5 is a schematic diagram showing an ultraviolet control unit of the sanitizing device for a handheld bidet sprayer.

FIG. 5 is a schematic diagram showing an ultraviolet control module used with the sterilizer and odor sensor 17. Ultraviolet control module can be provided as part of the controller 28 (FIG. 3) or can be provided as a separate circuit as depicted in FIG. 5. As shown in FIG. 5, the ultraviolet control module can include sensor and control circuit 38, UV controller-power module and driver circuit 39, UV controller 40, switch 41, and UV lamp 42. UV lamp 42 (which corresponds with UV light source 37 shown in FIGS. 1-3). The ultraviolet light can be generated as short wavelength UV light (UV-C), although anticipated wavelengths can be in the range of 10-350 nanometers, with a possibility of lower or higher wavelength UV light according to the anticipated target microbes. UV lamp 42 can be any convenient UV source, for example LED light or a germicidal light such as a 253.7 nm germicidal light. It is further anticipated that UV lamp 42 can be configured to provide multiple wavelengths of ultraviolet light. The ultraviolet light can be directed to the sprayer S to disinfect the sprayer S.

Figure 6:
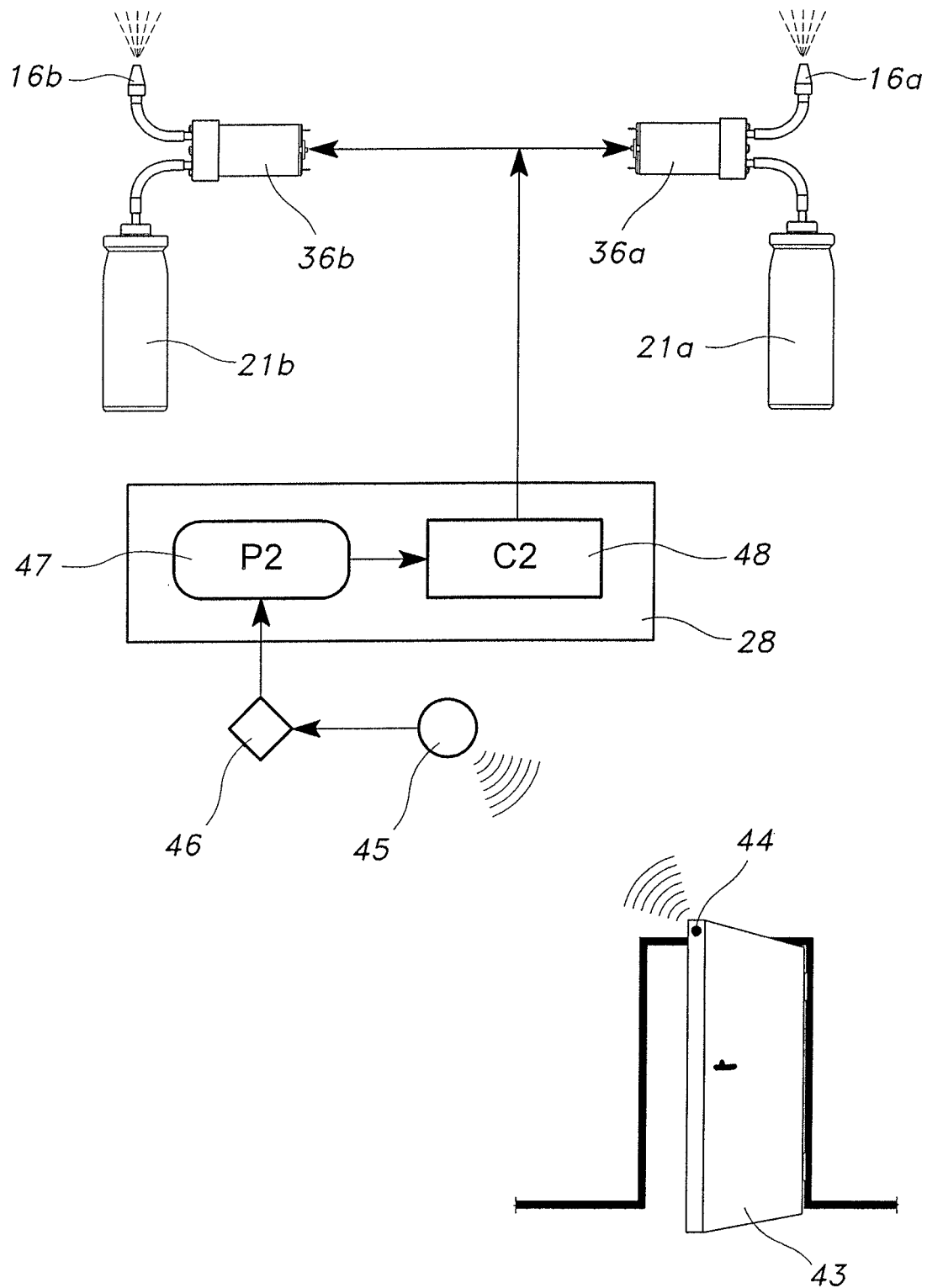
FIG. 6 is a schematic diagram showing the control module for activation of the sterilizer and odor detection device in response to a user entering or leaving the bath or toilet facility.

FIG. 6 is a schematic diagram showing activation of the sterilizer and odor detection device in response to a user entering or leaving the bath or toilet facility. This allows general activation, but also limits sensing of odor conditions to times when the toilet or bath space is occupied. Presence detection transmitter and sensors 44, 45, 46 are connected to presence detection circuit 47, and presence response controller 48, which are part of sensor and control circuit 38. The device can be programmed to discharge fragrance through fragrance outlet nozzles 16a and 16b, according to whether the user is present or optical sensor 13 detects the presence of bidet spray head or bidet shattaf 10.

Figure 7:
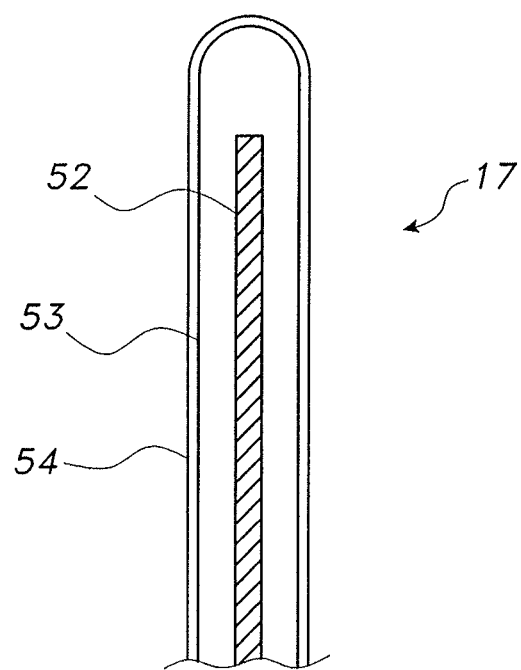
FIG. 7 is a schematic diagram of the sanitizing device for a handheld bidet sprayer, showing details of the odor sensor.

Optical sensor 13 is used by controller 28 to sense the presence or removal of bidet spray head or bidet shattaf 10. Odor sensor 17 detects patterns consistent with the presence of microbes or other sources of odors. Controller 38 causes discharge of sterilizer to treat bidet head 12 and to apply the sterilizer and fragrance chemicals to the user. In addition, UV light is projected by UV light source 37, which irradiates bidet head. It is also possible to configure UV light source 37 to apply UV energy to the user's skin. Odor sensor 17 is used to indicate the need for applying sterilizer and/or fragrance stored in chemical supply holder 18. Controller 38 may also control operation of a heater (not separately shown) so that removal of bidet spray head or bidet shattaf 10 or the presence of the user can be used to heat water for discharge. Alternatively, water can be heated in response to water flow FIG. 7 is a schematic diagram showing details of a non-limiting example of the construction of the odor sensor 17 depicted in FIGS. 1 4. Depicted are internal copper chemistry detector 52, an internal or external surface coating moisture absorbance material 53, and hollow porous rod 54, coated with moisture absorbance material 53. Moisture absorbance material 53 has an affinity for predetermined large molecules associated with odors, including molecules which are carried by moisture and molecules which are hydrophobic. The moisture absorbance material may, by way of non-limiting example, be of plural types, so as to separately detect different types of molecules. The detected molecules are used to indicate odoriferous conditions or to provide indications of a significant presence of microbes.

Other configurations can be used for moisture sensing, such as are commonly found on gas detectors and solid state alcohol sensors, and sensors used in alcohol detectors to detect interferents which may affect the sensing of the substances intended to be detected.

It is to be understood that the sanitizing device for handheld bidet sprayer is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A sanitizing device for a handheld bidet sprayer, comprising:
   a housing;
   a spray head mount on the housing;
   a control module within the housing;
   an optical sensor affixed to the housing, the optical sensor configured to detect the presence or absence of a bidet sprayer on the spray head mount;
   an odoriferous substance sensor affixed to the housing, the sensor configured to sense odoriferous conditions or indications of a significant presence of microbes;
   at least one chemical supply holder within the housing; and
   an ultraviolet light source located in the housing and directed to at least the spray head, wherein the ultraviolet light source can disinfect the spray head.

2. The sanitizing device as described in claim 1, wherein the ultraviolet light source comprises:
   an ultraviolet lamp; and
   a driver circuit for powering the ultraviolet light source, whereby, during a sanitation cycle, the ultraviolet light source provides surface sterilization of a handheld bidet sprayer.

3. The sanitizing device as described in claim 1, wherein the odoriferous substance sensor comprises:
   an internal copper chemistry detector having a surface coating moisture absorbance material with an affinity for large molecules associated with odors; and
   a hollow porous rod coated with moisture absorbance material having an affinity for large molecules associated with odors,
   wherein the large molecules associated with odors comprises molecules carried by moisture.

4. A handheld bidet system, comprising:
   a housing;
   a spray head mount on the housing;
   a handheld bidet having a sprayer removably mounted on the spray head mount;
   a control module within the housing;
   an optical sensor affixed to the housing, the optical sensor configured to detect the presence or absence of a bidet sprayer on the spray head mount;
   an odoriferous substance sensor affixed to the housing, the sensor configured to sense odoriferous conditions or indications of a significant presence of microbes; and
   at least one chemical supply holder within the housing.

5. The handheld bidet system as described in claim 4, wherein the housing further comprises:
   an ultraviolet light source;
   an ultraviolet lamp;
   a driver circuit for powering the ultraviolet light source, whereby, during a sanitation cycle, the ultraviolet light source provides surface sterilization of a handheld bidet sprayer.

6. The handheld bidet system as described in claim 4, wherein the odoriferous substance sensor comprises:
   an internal copper chemistry detector having a surface coating moisture absorbance material having an affinity for large molecules associated with odors; and
   a hollow porous rod coated with moisture absorbance material having an affinity for large molecules associated with odors,
   wherein the large molecules associated with odors comprises molecules carried by moisture.

* * * * *